United States Patent [19]
Koch et al.

[11] Patent Number: 5,962,756
[45] Date of Patent: Oct. 5, 1999

[54] NATURAL CAROTENOID CONCENTRATES FROM PLANT MATERIAL AND A PROCESS FOR PREPARING THE SAME

[75] Inventors: Lehel Koch; Matits Sándor; Tóth Kálmán; Pataki Attila, all of Budapest, Hungary; Borets Serghei Victorovich, Kishinau, Rep. of Moldova

[73] Assignee: Motiv Trading Joint Stock Company, Budapest, Hungary

[21] Appl. No.: 09/051,907

[22] PCT Filed: Oct. 8, 1996

[86] PCT No.: PCT/HU96/00057

§ 371 Date: May 4, 1998

§ 102(e) Date: May 4, 1998

[87] PCT Pub. No.: WO97/15554

PCT Pub. Date: May 1, 1997

[30] Foreign Application Priority Data

Oct. 27, 1995 [HU] Hungary ................................. 9502943
Aug. 9, 1996 [HU] Hungary ................................. 9502943

[51] Int. Cl.⁶ .......................................................... C07C 7/14
[52] U.S. Cl. ............................................ 585/351; 585/803
[58] Field of Search ....................................... 585/351, 803

[56] References Cited

U.S. PATENT DOCUMENTS

| 5,310,554 | 5/1994 | Haigh ........................................ 424/439 |
| 5,378,369 | 1/1995 | Rose et al. .............................. 210/637 |
| 5,714,658 | 2/1998 | Heidlas et al. .......................... 585/351 |

FOREIGN PATENT DOCUMENTS 2219965  9/1974  France .................................... 424/439

OTHER PUBLICATIONS

Koch et al, Chem. Abstracts, vol. 115, No. 239,702k, 1991.

*Primary Examiner*—James H. Reamer
*Attorney, Agent, or Firm*—Mathews, Collins, Shepherd & Gould, P.A.

[57] ABSTRACT

Chromoplasts and/or chloroplasts are isolated from plant material. This wet mass is digested in aqueous medium with pectin- and/or protein-cleaving enzymes, insoluble substances are removed, and a carotinoid-rich sediment is obtained after acidifying the separated colloid disperse system. The sediment is heated at alkaline pH with aqueous ethanol or isopropyl alcohol to remove the major part of cleaved proteins, lipides and other accompanying substances. The sediment with enriched carotenoid content is mixed with antioxidants and, if desired, dried, providing a carotenoid concentrate free of toxic solvent residues.

20 Claims, 1 Drawing Sheet

NATURAL CAROTENOID CONCENTRATES FROM PLANT MATERIAL AND A PROCESS FOR PREPARING THE SAME

FIELD OF THE INVENTION

The present invention relates to carotenoid concentrates obtained by processing chromoplasts and chloroplasts isolated from plant material and to a process for preparing the same.

BACKGROUND OF THE INVENTION

Carotenoids as referred to herein are a group of unsaturated hydrocarbons containing isoprene units or their derivatives substituted by various functional groups and the lipid addition compounds of the same.

It is well known that a healthy diet involves the consumption of appropriate amounts of high quality vegetables and fruits. Beside the different ingredients of these foodstuffs carotenoids are essential components for maintaining the health of the organism. Carotenoids, are highly efficient antioxidants, capturing the noxious free radicals continuously generated in the human organism. In addition, some carotenoids possess provitamin functions.

Beyond the provitamin function the main task of carotenoids is to inactivate the free radicals formed in increasing amounts in the human organism due to increased environmental hazards such as smoking, enhanced ultraviolet irradiation, air pollution, etc. However, even the best diet is unable to provide a sufficient continuous carotenoid supply which according to the data of various scientists may amount in the case of adults to a daily dose of 6–15 mg, so the need to apply carotenoid compositions as dietary supplements becomes ever more urgent.

Epidemiological surveys and other experimental data demonstrate that the incidence of morbidity and mortality due to various forms of cancer is lower in regions and in populations where vegetable and fruit consumption is high. The data show that this diet provides a sufficient carotenoid supply suggesting that carotenoids may have a prophylactic effect in preserving health.

As it is rather difficult, sometimes even impossible to provide a continuous carotenoid supply with the diet, there is an arising need to supplement the diet with carotenoid compositions prepared from various sources, and to ensure the required carotenoid supply in this way.

It has to be stressed that continuous carotenoid intake is a prerequisite of optimal efficacy. Free radicals are generated continuously in the organism thus they also have to be detoxicated continuously. This can only be achieved with a sufficient level of antioxidants in the organism. Carotenoids are not the only compounds which possess antioxidant properties, for example, tocopherols are also antioxidants. However, carotenoids are essential and together with tocopherols they even exert synergistic activity.

As a conclusion, carotenoids should be present in the human organism continuously and in suitable plasma levels to protect the organism prophylactically against abnormal processes induced by free radicals. As this effect is prophylactic, the regime has to be designed accordingly, i.e. the supplantation of the diet with carotenoids should be continuous.

Considering the above background the carotenoid compositions applied as continuous diet supplements, medications or eventually drugs (as vitamin preparations) should satisfy the following requirements:

a) the carotenoid spectrum should be similar to that of the human blood plasma, which is the following according to literature:

| | |
|---|---|
| alpha-carotene | 0.12–0.15 $\mu$mol/l, |
| beta-carotene | 0.40–0.80 $\mu$mol/l, |
| xanthophyll (lutein + zeaxanthine) | 0.28–0.35 $\mu$mol/l, |
| lycopene | 0.49–0.74 $\mu$mol/l, | b) the raw material used for preparing the composition should not represent any toxicological hazard, i.e. it cannot cause any nutritional health problem;

c) the manufacturing process should be devised in a way to ensure that the final product excludes toxic contaminants (solvent residues for instance), as the composition will be used continuously;

d) the composition should have sufficiently high active ingredient content to avoid administering large doses of the medication or dietary supplement [accordingly the carotenoid concentration stated in point a) should be increased at least 10 to 100 fold. Consequently it is our aim to prepare a product with a concentration of 50,000–100,000 m/kg from carrots with a carotene content of 100–200 mg/kg.

On the basis of the bioavailability of carotenoids to satisfy a daily carotenoid requirement of 10–15 mg/kg an adult would have to consume daily about 1 to 2 kg of carrots and tomatoes. Naturally this would induce adverse dietary side effects, such as excessive carbohydrate consumption, bad palatability and unbalanced complex diet. Furthermore, independently from the aforementioned aspects, to provide satisfactory carotenoid levels with adequate vegetable and fruit supplies would be limited by regional availability and financial constraints.

Summing up the aforementioned factors, the manufacturing and use of a suitable carotenoid composition would provide significant advantages.

The advantage of this invention should be appreciated if it is considered that the carotene content of prepared (processed or cooked) foods is rather low: 7,5–8,1 mg/100 g of alpha- and beta-carotene [M. S. Micozzi et al., J. Nat. Cancer. Inst., 82, 282–285 (1990); and Heinonen et al., J. Agric. Food Chem., 37, 655–659 (1989)], while that of the raw, uncooked carrot amounts to 150–200 mg/kg. Significant losses in carotene can be avoided with this new preparation which also has a much higher rate of absorption and bioavailability.

STATE OF THE ART

The properties of known products and the processes for manufacturing the same differ significantly from the product and process of the present invention.

U.S. Pat. No. 3,206,316 discloses water soluble or water dispersable compositions prepared most probably from synthetic carotenoids. Chlorinated solvents are used in the process which are avoided with the process of present invention.

WO 86/04059 refers to a process wherein the juice, obtained after mechanical milling and pressing of the carrots, is treated with pectin-degrading enzymes and concentrated by ultrafiltration. The residue is utilized in the form of a wet concentrate or in dried form. Chromoplasts are not purified further, consequently the concentration in the final product amounts to 500–600 mg carotene/100 g product, while in the product according to the present invention the carotene content is 10 to 20 fold higher, e.g., from 2500 to up to 10,000 mg carotene/100 g product.

WO 92/18471 refers to the extraction of carotenoids from natural sources, mostly from carrots, to obtain a product practically identical to that referred to in WO 86104059. In the chromoplasts (obtained as a final product) precipitated with calcium chloride as an auxiliary material, the carotene concentration amounts to 12.44 mg/g dry material, while the process according to the present invention provides a tenfold concentration increase.

U.S. Pat. No. 2,412,707 refers to an oily emulsion prepared by cooking (heating) a wet raw material in an edible (cooking) oil. Neither the process nor the product are comparable to the object of the present invention.

U.S. Pat. No. 2,412,707 discloses a process wherein plant chromoplasts were isolated in aqueous suspension and subsequently precipitated by coagulation. The chromoplasts were neither purified, nor processed, and no attempts were made to increase the carotene concentration.

Ind. Eng. Chem., 46, 2279 (1954) refers to a complex extraction process wherein carotenoids are selectively isolated from the raw material by using various solvents. In the course of this process undesirable solvents, such as hexane, heptane, acetone, etc. are used. This procedure is contrary to our purification process according to which the active ingredients are not leached from the chromoplasts but instead, the additional components and inactive ingredients are removed from the chromoplasts with a non-toxic, alkaline solution. As used herein, the term "toxic solvents" includes hexane, ketones including acetone, aprotic solvents such as carbon tetrachloride (chloroform) or chlorinated or halogenated hydrocarbons, a polar and aromatic solvents such as benzene or toluene, and other solvents that are known to create nutritional problems or adverse health effects when chronically consumed by humans, excluding aliphatic carboxylic acids or phosphoric acids.

There is also a process wherein carotenoids are isolated from palm oil. Here carotenoids are dissolved in palm oil. The palm-oil is heated (cooked) with alkalies and thereafter carotenoids are extracted with hexane.

FR-A-2 219 965 discloses principles of a method, wherein pigments are separated from plants by a combination of mechanical and enzymatic processes. According to said method the chloroplast fraction isolated from mechanically ground plants is digested with enzymes to degrade the cellulose lamellas, and the digested slurry is diluted with water to promote degradation products. Pigments, e.g., chloroplasts and carotenoids, are separated by centrifugation. The product obtained as a sediment should contain many cell debris and other insoluble components. Particular working examples and any data relating to the components of products are missing.

Hungarian Patent No. 208 669 (reviewed in Chem. Abstr. Vol. 115, No. 22, page 496, 239702k; 1991) discloses a method for preparation of a beta-carotin concentrate from plants, wherein a slurry of chromoplasts is subjected to lactic acid fermentation under anaerobic conditions to achieve the flocculation of chromoplasts by acidification at about pH 4.5 to 4.1. The acidic slurry is concentrated on a separator, and the concentrated sediment is alkalized to pH 9.5 and digested with pancreatin and pancreatic lipase. Ethanol is added when the pH reaches 7.5 to 7.0, and the mixture is refluxed to precipitate the carotenoids. The carotenoid content of the vacuum dried precipitate is in the range of 6 to 9% (w/w).

Hungarian Patent Application P 93 03605 refers to a process wherein the chromoplast fraction is made to flocculate in the press-liquid of mechanically processed (milled, pressed) carrots. Then a significant portion of the protein content is digested with a protease enzyme, and the precipitate formed at pH 3.5–4.5 and containing the carotenoids is dried.

SUMMARY OF THE INVENTION.

In the course of experiments it was found that compositions with advantageous properties can be prepared by refining, i.e. concentrating the carotenoid content of chloroplasts and chromoplasts isolated from plant materials.

The process is based on the observation that the Carotenoids in chromoplasts, bound to lipoproteins or forming adducts with various lipids, form particles in the colloid range. If these lipids or a part of them are removed by a lipophilic solvent, thereby disrupting the lipoprotein/lipid system, the carotenoid concentration in the residue can be increased several fold without using undesirable or highly toxic solvents (for example hexane, or chlorinated hydrocarbons), residues of which, even in trace amounts, are highly noxious; their chronic consumption, together with the carotenoids (as they are similarly lipophilic as carotene) results in a continuous migration to the target cells and tissues where they cause greatest damage by being accumulated and not eliminated.

In the process of the present invention no chlorinated solvents are used, as in the process according to U.S. Pat. No. 3,206,316, nor aprotic, a polar solvents, such as hexane.

DETAILED DESCRIPTION OF THE INVENTION.

The present invention relates to a product with a chromoplast/lipoprotein complex enriched to various carotenoid concentrations and having the following properties:

a) the carotenoid concentration is increased 400 to 500 fold compared to the carotenoid concentration of the raw material and two to fifteen fold compared to the carotenoid content of the crude chromoplast precipitate;

b) the concentration is increased by cleaving the protein/lipid component of the lipoprotein complex and removing the salts of peptides, amino acids and fatty acids by dissolution from the side of carotenoids;

c) the complex is cleaved by considering the solubilities of degradation products which are soluble at a rate several orders of magnitude higher in a water/alcohol (ethanol, rectified alcohol, isopropyl alcohol) mixture. Thus, no toxic solvent residues having an $LD_{50}$ higher than that of ethanol are retained in the final product;

d) the carotenoid spectrum of the product, obtained by processing chromoplasts isolated from appropriately selected raw materials, e.g. carrots or tomatoes, satisfies the general requirements, such as similarity to the carotenoid spectrum of the human blood plasma, in an optimal way.

The invention further relates to a process for preparing a product with the aforementioned properties which comprises isolating the chromoplasts containing the carotenoids by known methods, preferably from carrots or tomatoes, separating them with sedimentation or centrifuging, then cleaving the lipoproteins by enzymatic treatment of the chromoplast fraction. The partially purified crude carotenoid fraction is precipitated by acidifying the liquid phase retained after the removal of the accompanying substances, and the precipitate, after addition of an alkali solution is refluxed several times with fresh aqueous ethanol to remove alkali salts of peptides, amino acids, fatty acids, etc. is liberated during the cleavage of the complex. The suspension of the carotenoid concentrate is slightly acidified by addition of sodium dihydrogen phosphate and citric acid, and the sedimented or centrifuged product is mixed with antioxidants and thereafter, if desired, dried.

The enzymatic cleavage is preferably performed by homogenizing the chromoplast and/or chloroplast fraction isolated from the plant material with a three to five fold amount of water, calculated for dry material. The pH of the homogenizate is adjusted to about 8.5 with sodium hydroxide solution, and then the mixture is submitted to enzymatic digestion with a protein degrading enzyme (having preferably also some lipase activity), such as pancreatin, for 2–3 hours at 37–38° C., while the pH is continuously readjusted to the initial value by repeated addition of sodium hydroxide solution. After the enzymatic digestion the mixture is centrifuged at 1200 g, the brown gelous precipitate is separated. The liquid phase or "supernatant" or "centrate" is then acidified to pH 3.5–4.0, preferably with an acid acceptable in the food industry. It is preferred to centrifuge the precipitated material at 3000 g.

The carotenoid fraction is further refined (purified, concentrated) by suspending the precipitate obtained by centrifuging the acidified mixture after enzymatic digestion in a 60:40 to 80:20, preferably 70:30 v/v mixture of ethanol-water, adding 35 g of sodium hydroxide (calculated for 1 kg of dry material) preferably as a 10–35% w/w solution in water or the above mixture and refluxing the mixture for 2 hours. The insoluble sediment is centrifuged, and the procedure is repeated by adding the same amount of sodium hydroxide solution.

At the first alkaline treatment preferably an eight-fold volume of 70:30 ethanol-water mixture, and at the second alkaline treatment a five-fold volume of 80:20 ethanol-water mixture is used.

After the second 2-hour reflux centrifugation is repeated, the sediment is resuspended in a four-fold solvent mixture (without addition of alkali), and refluxed for a third time. Half an hour before completing the refluxing a solution containing 30 g of sodium dihydrogen phosphate ($NaH_2PO_4$) and 200 g of citric acid (calculated for 1 kg of dry material) is added. The solution is prepared by dissolving said compounds in a mixture of ethanol-water identical as used above [i.e.(80:20)].

After centrifuging usually 45–50% of the starting dry substance is recovered, while the rest is leached as sodium salt of peptides, amino acids, fatty acids, etc. Loss in carotenoids is minimal, and is mostly dependent on handling skills at the separations.

By the end of the aforementioned operations the carotene content of the chromoplast fraction is twice as high or even slightly higher than that of the starting material.

In this way the processing of fresh carrots with a carotene content of 150 mg/kg results after completed work-up of the chromoplast precipitate in a dry material with a carotene content of 7.5–8.5%.

By repeated alkaline treatment(s) the carotene concentration may be further increased over 10–15%. Approaches to attain even higher concentrations is economically questionable due to high solvent, energy and manpower requirements and even loss of carotenoids during the separations.

After the repeated alkaline treatments a 80:20 v/v ethanol-water solution is added in 6fold amounts, calculated for the dry material obtained after separation, and the mixture is refluxed under stirring for 2 hours.

Then the pH is adjusted to 7.0–7.2, in about the neutral range by adding necessary amounts of sodium dihydrogen phosphate and citric acid to the stirred mixture.

The centrifuged substance is mixed (kneaded) with tocopherols and ascor-byl palmitate and dried in this alcohol-wet form at a temperature not higher than under 60° C., but may be utilized also in wet form.

The sieved dry powder is vacuum-packed.

Chloroplasts obtained from photosynthesizing plant organisms can be processed similarly. However, in this case the degradation products of chlorophyll, such as pheophitine and pheophorbide should be removed with utmost care if the final carotenoid concentrate is designed for human consumption.

Significant new aspects of the process of the invention:

cellular elements of chromoplasts and chloroplasts are transferred into liquid phase (press-liquid, decanter-separator liquid) by mechanical processing partly performed in alkaline medium;

chromoplasts in the liquid phase or in the suspension are denatured by adjusting the pH or by heat-treatment, or by the combination of both, and as a result they are precipitated from the liquid phase;

the precipitated flocculi are separated (decantation, separation), the water soluble components are removed, and the carotenoid concentration in the separated flocculi is already significantly increased compared to the starting material;

chromoplasts and chloroplasts containing the coloured substances, including the carotenoids, are lipoprotein complexes with a very high lipid content which holds the carotenoids (which are practically insoluble in water and poorly soluble even in organic solvents) in colloid solution, and transport them within the organism. A part of the lipids in the complex is retained in the product, and promotes the bioavailability of carotenoids.

The new inspiration is, that not the carotenoids have to be removed from accompanying substances, but the accompanying substances should be removed from the carotenoids in largest possible proportions. This may be realized by cleaving the lipoprotein complex in alkaline medium, transferring the major part of the lipids in the form of their sodium salts into the aqueous ethanol solution and removing them.

By choosing the appropriate raw materials, preparing crude carotenoid concentrates from them, then mixing the same, products may be obtained with a carotenoid spectrum which satisfies the requirements of the human organism and which is similar to the carotenoid spectrum of the human blood plasma.

The aforementioned advantages may be attained by avoiding the use of toxic solvents usually applied for the dissolution of carotenoids. As a consequence the by-products and wastes generated in the course of the process do not pollute the environment, are biodegradable and mostly may be utilized as food or feed additives.

The following examples illustrate the aforementioned product and the process for preparing the same in detail without limiting the scope of the invention. The % values, if not otherwise stated, relate to w/w.

The assay of carotenoids was performed according to the following methods:

a) beta-carotene was assayed by the modified spectrophotometric Booth method [M. A. van der Meer et al. (Wageningen), Z. Lebensmittel Unter-such. und Forschung, 185, 461–467 (1987)];

b) the carotenoid spectrum was determined by high performance liquid chromatography (HPLC) using Waters 600 Multisolvent Delivery System (Waters, Milford, USA) with reverse-phase LiChrosorb RP-18 (10 μm, 250×4.6 mm) and Spherisorb ODS (5 μm, 250×4,6 mm) columns, acetonitrile-methanol-tetrahydrofuran (75:15:10 v/v) mixture as eluent and a photodiode sensor (Photo Diode Array Detector 990 (DAD), Waters, Milford, USA) as detector in the wavelength range of 190–800 nm. Pure reference substances were used as internal standards.

EXAMPLES

Figure 1:
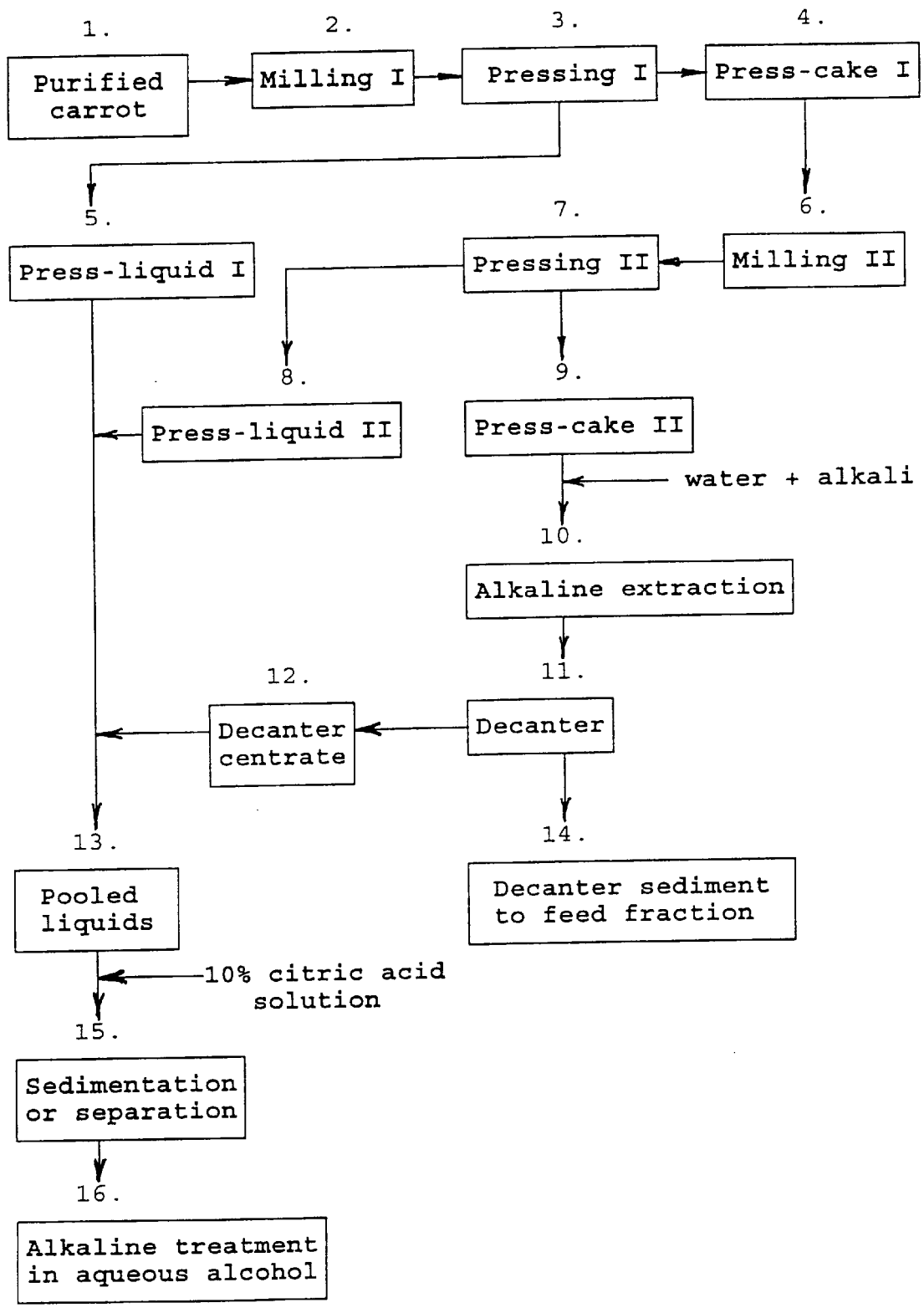
FIG. 1 showns a method known in the art for the pretreatment of the raw material.

Example 1
Preparation of a Concentrate with 5% Carotenoid Content from Carrots (*Daucus carota*)

1000 kgs of defoliated carrots (carotenoid content 180–200 mg/kg carrot body) were processed by a method known in the art according to the scheme shown on FIG. 1. The purified and washed carrot bodies were milled, pressed, the residual cake was again milled, homogenized with water and repeatedly pressed, then the repeatedly milled and pressed fibrous cake was extracted in a third step with sodium hydroxide solution at pH 8.5, and the residue was separated from the extract (decanter centrate) on a decanter centrifuge. The press liquids and the decanter centrate were pooled, and the pooled solution was acidified with 10% citric acid solution to pH 4.0. The chromoplasts were flocculated, and left to settle.

220 litres of sediment, which could be pumped, was separated by decantaion, the pH was adjusted to 8.5 with 10% sodium hydroxide solution and the proteins were digested at 37° C. under vigorous stirring by adding a suspension of 100 g of pancreatin in 10 litres of water to the stirred mixture and readjusting continuously the decreasing pH with 10% sodium hydroxide solution. Treatment was continued for 3 hours, then the mixture (pH 8.5) was separated by a decanter centrifuge from the insoluble particles which were not in colloid solution. The sediment separated by the decanter centrifuge can be mixed to a feed fraction before drying.

The decanter centrate, containing also the carotenoids, was acidified to pH 4.0 with 10% citric acid solution, and the precipitated flocculi were isolated by separation.

The separator sludge containing 16–18% of dry substance with 2.5% of carotenoid content (calculated for the dry material) and having a wet weight of 45–50 kg, was mixed with 90 litres of a 80:20 v/v ethanol-water mixture, then 3 litres of 10% sodium hydroxide solution were added. This mixture was refluxed for 2 hours under vigorous stirring.

The hot mixture was separated and the separator sediment (having a wet weight of 28–30 kg) was subjected to repeated alkaline treatment by adding 50 litres of aqueous ethanol (80:20) and 2 litres of 10% sodium hydroxide solution, then refluxing the mixture for 2 hours. The separation was repeated to yield 16–20 kgs of wet precipitate.

The wet precipitate was first refluxed for one hour with 40 litres of aqueous ethanol as used above. During this procedure a 3:1 mixture of 10% aqueous solutions of citric acid and sodium dihydrogen phosphate were added in amounts to obtain an approximately neutral pH (7.0–7.2). This requires usually 300 g of citric acid and 100 g of sodium dihydrogen phosphate.

After separation 14–16 kg of sediment with a dry material content of 3.2 kg, including 0.19 kg of carotenoids was obtained.

To this sediment 150–300 g of an antioxidant mixture (2:2:1 w/w mixture of alpha-tocopheryl acetate, alpha-tocopherol and ascorbyl palmitate) was added. The mixture was thoroughly mixed (kneaded) and dried in vacuum at a temperature not higher than 50° C.

Specification of the dried final product:

| | |
|---|---|
| mass | 3.4 kg, |
| carotenoid content | 5.5%, |
| drying loss | max. 5% (at 105° C.; 3 hours), |
| colour | reddish-brown, |
| carotenoid spectrum: | 60–65% beta-carotene, |
| | 28–30% alpha-carotene and |
| | 5–10% other carotenoids. |

Stable in vacuum or under a protecting gas for min. 1 year.

Example 2
Preparation of a Concentrate with a Carotenoid Content of 7–8%.

The procedure described in Example 1 was applied, however carrots with a carotenoid content of 220–250 mg/kg were used as raw material, and the protein cleavage was performed with a bacterial (*B. subtilis*) protease.

Final product: 3 kg of reddish-brown dry powder or particles with a carotenoid content of 7.5–8.0%, having similar carotenoid spectrum as in Example 1.

Example 3
Preparation of a Concentrate with a Carotenoid Content of about 10%.

A raw material as used in Example 2 was processed. The two alkaline treatments were supplemented with a third one, using identical amounts of solvent and alkali as in the second alkaline treatment. Then, according to Example 1, the wet precipitate was refluxed with 40 litres of an 80:20 ethanol-water mixture for one hour, thereafter the mixture was neutralized according to Example 1, the sediment was separated, mixed with the antioxidant mixture and dried in vacuum.

Final product: 1.6 kg of reddish-brown dry product;

drying loss max. 6%, carotenoid content min. 10.5% (0,17 kg), the carotenoid spectrum is as in the former Example.

Example 4
Preparation of a Lycopene-rich Concentrate from Carrots and Tomatoes The chromoplasts containing the carotenoids were isolated separately from carrots and tomatoes, thereafter the pooled material was processed (refined).

500 kgs of washed and defoliated carrots (carotenoid content 220 mg/kg carrot body) were processsed. The juice was obtained according to the scheme shown on FIG. 1. The chromoplasts flocculated at pH 4.0 (10% citric acid solution) were permitted to settle and were separated by decantation. The dilute sludge with a dry material content of approximately 8% was concentrated in a separator yielding a sediment with a dry material content of 16–20%. This is subjected to alkaline treatment without prior protein cleavage. To 20–25 kg of the wet sediment a 3fold (about 75 kg) ethanol-water (80:20) mixture and 1.5 litres of 10% sodium hydroxide solution were added. The mixture was refluxed for 2 hours, the hot mixture was separated, then the treatment of the sediment was repeated. After two alkaline treatments the precipitate obtained by separation or centrifugation was washed with aqueous ethanol and neutralized according to Example 1. The precipitate separated after 2 hours of reflux is the first component of the final product.

Separately from the carrots 1000 kgs of tomatoes were processed. The juice was separated by known methods with straining, and the juice containing 7% of dry material was concentrated to obtain a concentrate with a dry material content of 20%. The concentrate was treated three times with ethanol. First it was refluxed for two hours with a 2fold volume of 96% pure ethanol (about 500 litres), then the alcoholic phase was separated, and the treatment was repeated twice with aqueous ethanol (80:20). During the third treatment 3 litres of 10% sodium hydroxide solution were added to the stirred refluxed mixture. The residue obtained after the third treatment, consisting mainly of pectin, polysaccharide and fibers, was added to a feed composition before drying. The alcoholic extracts were pooled, the pH was adjusted to 7.0–7.5 with a mixture of citric acid/sodium dihydrogen phosphate solutions as described in Example 1, and the mixture was evaporated. The alcohol was recovered, and 10 litres of a concentrate were obtained, which was mixed as the second component to the wet sediment obtained by the processing of carrots (7–8 kg), homogenized with 5% antioxidants and dried in vacuum.

Final product: 3.6 kg of reddish-brown dry material,

| | |
|---|---|
| drying loss | max. 5%, |
| carotenoid content | min. 5.5%, |
| carotenoid spectrum: | lycopene 1.8%, |
| | beta-carotene 2.0%, |
| | alpha-carotene 1.2%, |
| | lutein + others 0.5%. |

The product is characteristic for its high lycopene content.

Example 5

Preparation of a Product with High Lycopene Content

Carrots were processed as described in Example 4.

3000 kgs of tomatoes were processed, the pectin content of the tomato juice was digested with pectinase, isolated from an Aspergillus culture at pH 4.0 by a method known in the art. After pectin digestion the dilute juice was concentrated in vacuo from a dry material content of 7% to 30% to yield 540 kg of a concentrate, which was treated with ethanol. The first treatment was performed with 3fold volume of 96% pure ethanol, the next two ones with an 80:20 ethanol-water mixture. Each alcohol treatment was performed by refluxing for 2 hours. During the third alcoholic treatment 8 litres of 10% sodium hydroxide solution were added to the stirred and refluxed solution. In the course of the alcoholic treatments the alcoholic solutions were separated from the insoluble parts. (Alcohol was removed from the lycopene-free material obtained after the third alcoholic treatment, dried and added to a feed composition).

The pH of the pooled alcoholic solutions was adjusted to 7.0–7.5 by addition of a mixture of citric acid/sodium dihydrogen phosphate solutions as described in Example 1, the neutralized mixture was concentrated to 20 liters, and the alcohol was recovered. The concentrate was homogenized with the wet sediment of the carrot procedure, then mixed with 5% of antioxidants (calculated for dry material) and dried in vacuum.

Final product: 6.2 kg of reddish-brown dry material,

| | |
|---|---|
| drying loss | max. 5%, |
| carotenoid content | min. 5.5%, |
| carotenoid spectrum: | lycopene 3.0%, |
| | beta-carotene 1.2%, |
| | alpha-carotene 0.6%, |
| | other carotenoids 0.7%. |

The product is characteristic for the similar content of lycopene:carotene.

Example 6

Carotenoid Concentrate from Carrots and Broccoli 1000 kgs of carrots and 1000 kgs of broccoli were processed, and juices were prepared according to the scheme shown on FIG. 1.

The juices were heated to 56° C., the pH was adjusted to 4.0 with 10% citric acid solution, then the solutions were cooled to 20–25° C. and the precipitated chromoplast and chloroplast flocculi were settled.

The sediment was concentrated in a separator to yield a wet sediment with a dry material content of 20%. To 22 kg of dry material (about 90 kg of wet sediment) 180 litres of aqueous ethanol (80:20) were added under vigorous stirring, the pH was adjusted to 9.5 by the addition of 6 litres of 10% sodium hydroxide solution and the mixture was refluxed for 2 hours. The hot mixture was separated. This treatment was repeated three times. After each treatment the volume of the sodium hydroxide solution and the solvent was reduced proportionally to the decrease of the dry material content. Tentative amounts (calculated for dry material): 8–10fold volumes of aqueous ethanol (80:20) and 2.25–3.5% of sodium hydroxide.

The residue of the fourth alkaline treatment was suspended in 45 litres of aqueous ethanol (70:30), refluxed and neutralized according to Example 1. After separation 4.1 kg of sediment was obtained, which was mixed with 5% of antioxidant mixture, dried in vacuo at a temperature not higher than 50° C. After drying 3.5 kg product was obtained containing significant amounts of dihydroxycarotenoids (luteine, zeaxanthine).

Final product: greenish-brown dry material,

| | |
|---|---|
| drying loss | max. 5%, |
| carotenoid content: | min. 6.5%, |
| carotenoid spectrum: | beta-carotene 3.2%, |
| | alpha-carotene 1.5%, |
| | lutein + zeaxanthine 1.0%, |
| | lycopene 0.4%, |
| | other carotenoids 0.4%. |

Example 7

Preparation of a Concentrate with a Carotenoid Spectrum Similar to that of Blood Plasma The products of Examples 4, 5 and 6, mixed with antioxidants, are homogenized in alcohol-wet form in a proportion of 1:2:1, then the mixture is dried in vacuum.

Final product: greenish-brown dry material,

| | |
|---|---|
| drying loss | max. 5%, |
| carotenoid content: | min. 6.2% |
| carotenoid spectrum: | lycopene 32.9%, |
| | beta-carotene 30.5%, |
| | alpha-carotene 21.7%, | lutein + zeaxanthine 11.6%,
other carotenoids 3.3%.

The lycopene and dihydroxy-carotenoid (luteine and zeaxanthine) contents of the product are in good agreement with desirable blood plasma levels. The product can not only ensure a satisfactory alpha- and beta-carotene supply, but with the presence of lycopene and dihydroxy-carotenoids, both having high antioxidant properties, further improves the advantages of the product.

Example 8
Preparation of a Concentrate with a Carotenoid Spectrum Similar to that of Blood Plasma The dried products of Examples 4, 5 and 6 were mixed in mass proportions of 1:2:1, as given in Example 7. The carotenoid spectrum of the product is similar to that of the product obtained in Example 7.

Example 9
Processing of Dunaliella or Blakeslea spp.

The biomass of Dunaliella or Blakeslea spp., obtained from natural sources or from fermentation cultures, was concentrated to a dry material content of 8–10% by sedimentation or centrifugation. The carotenoid content of the dry material in the concentrate amounted to 2%. The mass was heated to 100° C. by blowing saturated steam of 3 bar into it. The temperature was maintained for 10 minutes sby a continuous steam flow, when the mass was plasmolyzed.

The pH of the plasmolysate was adjusted to 11 by addition of sodium hydroxide in an amount corresponding to about 5% of the dry material dissolved in a 20fold volume of an isopropanol-water (70:30, v/v) mixture, the mixture was refluxed under stirring for 2 hours, then the hot mixture was subjected to separation, isolating the sediment and the liquid phase.

To the wet sediment 2 volumes of an isopropanol-water (80:20) mixture and 0.08 volumes of 10% sodium-hydroxide solution were added, then the mixture was refluxed for 2 hours and the separation was repeated.

This teatment was repeated two more times.

To the wet sediment obtained after the fourth treatment 2 volumes of an isopropanol-water (80:20) mixture were added, and after refluxing for one hour the hot sludge was neutralized, then filtered or centrifuged as described in Example 1.

The filter cake or centrifuge sediment, obtained after neutralization and separation was mixed with antioxidants as described in Example 1 and finally dried in vacuum.

The dry, reddish-brown product has the following specification:

| | |
|---|---|
| dry material content | 94–96%, |
| crude protein (N × 6.25) | 18–22%, |
| crude fibers | 5–6%, |
| sulfated ash | 20–25%, |
| non-protein accompanying components | 8–10%, |
| lipids*) | 32–46%, |
| carotenoid content of them | 20–25%. |

*)lipid-like substances soluble in mixtures of chloroform and methanol (non-saponifyable lipid fraction).

The carotenoid spectrum of the product depends on environmental factors of the starting cultures or fermentation conditions, but the carotenoid content of the product is not less than tenfold of the carotenoid content of the dry material in the starting plasmolysate, i.e. the enrichment is at least tenfold.

We claim:

1. A process for preparing a natural carotenoid product refined from impurities, the process comprising the steps of:
    i) providing a press liquid containing at least one of a chromoplast or chloroplast fraction isolated from a plant;
    ii) acidifying said press liquid to about the isoelectric point of chromoplasts or chloroplasts to provide a carotenoid-containing sediment;
    iii) treating said carotenoid-containing sediment in aqueous alkaline medium under controlled conditions with a pectin or protein-cleaving enzyme to provide a colloidal-carotenoid solution;
    iv) separating impurities as a sediment from the colloidal-carotenoid solution;
    v) acidifying the colloidal-carotenoid solution to provide a carotenoid-rich precipitate, whereby impurities are left remaining in the liquid phase;
    vi) substantially neutralizing the carotenoid-rich precipitate and isolating the natural carotenoid product therefrom.

2. A process according to claim 1, wherein the step of acidifying the press liquid to (provide the carotenoid-containing sediment (step ii) is performed by adjusting the pH in a range between 3.0 and 8.5 to about the isoelectric point of chromoplasts or chloroplasts with addition of one or more acids selected from the group consisting of aliphatic carboxylic acids having from two to four carbon atoms, mono-, dihydroxy-di- and -tricarboxylic acids, and phosphoric acid; or salts thereof formed with alkali metals or alkali earth metals or hydroxides of alkali metals or alkali earth metals.

3. A process according to claim 1, wherein the step of acidifying (step v) is performed whereby the solution is heated to a temperature not higher than about 60° C. or cooled to a temperature not lower than about 5° C.

4. A process according to claim 1, wherein the carotenoid-rich precipitate provided pursuant to step v) or the carotenoid product isolated therefrom is mixed one or more times with aqueous alcohol.

5. A process according to claim 1, wherein the step of treating said carotenoid-containing sediment (step iii)) comprises using an aqueous solution of water and ethanol or water and isopropyl alcohol with a water content of 15–40% by volume and with a boiling point lower than 90° C.

6. A process according to claim 1, further comprising the step of mixing one or more of the carotenoid products with antioxidants and either drying the mixture by freeze-drying or vacuum-drying at temperatures lower than 60° C. or using it in wet form.

7. An improved process for isolating a carotenoid product from plant material containing at least one or more chromoplasts or chloroplasts, wherein the process comprises providing a crude carotenoid concentrate containing impurities, the improvement comprising the steps of:
    i) performing an alkaline treatment comprising mixing the crude carotenoid with an aqueous alcoholic solution at an alkaline pH and heating the mixture for a time period sufficient so that the carotenoids of the crude carotenoid concentrate are present in the aqueous solution in the colloidal disperse phase and the impurities may be removed from the crude carotenoid without the use of toxic solvents, and
    ii) neutralizing the mixture of crude carotenoid and aqueous solution and isolating the concentrated carotenoid product therefrom.

8. The process of claim 7, further comprising performing a plurality of alkaline treatments according to step i).

9. The process of claim 7, wherein the aqueous solution comprises water mixed with an alkali or alcohol selected from the group consisting of ethanol, isopropyl alcohol, rectified alcohol, and sodium hydroxide.

10. The process of claim 7, wherein the step of neutralizing the mixture comprises adding sodium dihydrogen phosphate or citric acid to the mixture.

11. The process of claim 7, wherein the step of performing an alkaline treatment comprises adjusting the pH of the mixture to about 8.0 to about 8.5.

12. The process of claim 7, wherein the step of performing an alkaline treatment (step (i)) comprises refluxing the mixture for less than four hours.

13. A natural carotenoid concentrate free of toxic solvent residues, containing at least 1.5 to 25 weight percent natural carotenoids prepared with the process of claim 7.

14. The process according to claim 7, further comprising mixing in predetermined proportions several wet or dry carotenoid products having different carotenoid spectra.

15. A mixture of carotenoid concentrates according to claim 14 prepared from a plurality of carotenoid-rich masses derived from plants including carrots, tomatoes, and broccoli.

16. A mixture comprising the carotenoid concentrate according to claim 7 and antioxidants.

17. The mixture of claim 16 wherein the antioxidants comprise tocopherols.

18. The concentrate according to claim 7, comprising about 10–30% alpha-carotene, about 22–65% beta-carotene, about 6–55% lycopene, and about 5–22% dihydroxy-carotenes.

19. A process for preparing a natural carotenoid product comprising the steps of:
  i) preparing a press liquid containing carotenoids;
  ii) acidifiing the press liquid to about the isoelectric point of chromoplasts or chloroplasts to precipitate the carotenoids and separating the precipitate as a first carotenoid-containing sediment;
  iii) digesting the first carotenoid-containing sediment with pancreatin at an alkaline pH of greater than 7.5 for a time period sufficient so that carotenoids are present in a colloid disperse phase defining a supernatant;
  iv) acidifying the supernatant to a pH of less than about 4.5 to separate a second carotenoid-containing sediment from the supernatant; and
  v) neutralizing the second carotenoid-containing sediment and isolating the natural carotenoid product therefrom.

20. A process according to claim 1, wherein the step of treating (step iii), comprises utilizing an enzyme selected from a protease of bacterial origin, including *B. subtilis*; fungal origin, including *Aspergillus oryzae*; plant origin, including papain; or animal origin, including pancreatin; at a pH range of between 4.5 and 11.

* * * * *